United States Patent
Buthe et al.

(10) Patent No.: US 9,428,740 B2
(45) Date of Patent: Aug. 30, 2016

(54) LIPASE-CONTAINING POLYMERIC COATINGS FOR THE FACILITATED REMOVAL OF FINGERPRINTS

(71) Applicants: Toyota Motor Engineering & Manufacturing North America, Inc., Erlanger, KY (US); Toyota Motor Corporation, Toyota-shi, Aichi-ken (JP); Regents of the University of Minnesota, Minneapolis, MN (US)

(72) Inventors: Andreas Buthe, Steinfurt (DE); Ping Wang, North Oaks, MN (US); Songtao Wu, Ann Arbor, MI (US); Hongfei Jia, Ann Arbor, MI (US); Masahiko Ishii, Okazaki (JP); Minjuan Zhang, Ann Arbor, MI (US)

(73) Assignees: Toyota Motor Engineering & Manufacturing North America, Inc., Erlanger, KY (US); Toyota Motor Corporation, Toyota-shi (JP); Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 14/643,445

(22) Filed: Mar. 10, 2015

(65) Prior Publication Data

US 2015/0175982 A1  Jun. 25, 2015

Related U.S. Application Data

(60) Continuation of application No. 13/757,978, filed on Feb. 4, 2013, now Pat. No. 9,012,196, which is a division of application No. 12/820,063, filed on Jun. 21, 2010, now Pat. No. 8,394,618.

(51) Int. Cl.
- *C12N 9/20* (2006.01)
- *C12N 11/08* (2006.01)
- *D06M 10/00* (2006.01)

(52) U.S. Cl.
CPC .............. *C12N 9/20* (2013.01); *C12N 11/08* (2013.01); *D06M 10/001* (2013.01)

(58) Field of Classification Search
None
See application file for complete search history.

(56) References Cited

U.S. PATENT DOCUMENTS

| | | | |
|---|---|---|---|
| 4,016,043 A | 4/1977 | Schuurs et al. | |
| 4,094,744 A | 6/1978 | Hartdegen et al. | |
| 4,098,645 A | 7/1978 | Hartdegen et al. | |
| 4,195,127 A | 3/1980 | Hartdegen et al. | |
| 4,195,129 A | 3/1980 | Fukui et al. | |
| 5,418,146 A | 5/1995 | Joo et al. | |
| 5,559,163 A | 9/1996 | Dawson et al. | |
| 5,770,188 A | 6/1998 | Hamade et al. | |
| 5,914,367 A | 6/1999 | Dordick et al. | |
| 5,919,689 A | 7/1999 | Selvig et al. | |
| H1818 H | 11/1999 | Potgieter et al. | |
| 5,998,200 A | 12/1999 | Bonaventura et al. | |
| 6,030,933 A | 2/2000 | Herbots et al. | |
| 6,150,146 A | 11/2000 | Hamade et al. | |
| 6,291,582 B1 | 9/2001 | Dordick et al. | |
| 6,342,386 B1 | 1/2002 | Powers et al. | |
| 6,599,627 B2 | 7/2003 | Yeo et al. | |
| 6,855,746 B2 | 2/2005 | Yoshitake et al. | |
| 6,875,456 B2 | 4/2005 | Delest et al. | |
| 6,881,711 B1 | 4/2005 | Gershun et al. | |
| 6,905,733 B2 | 6/2005 | Russell et al. | |
| 7,335,400 B2 | 2/2008 | Russell et al. | |
| 7,632,793 B2 | 12/2009 | Lang | |
| 7,932,230 B2 | 4/2011 | McDaniel | |
| 7,939,500 B2 | 5/2011 | McDaniel | |
| 8,388,904 B1 | 3/2013 | McDaniel et al. | |
| 8,394,618 B2 | 3/2013 | Buthe et al. | |
| 8,497,248 B2 | 7/2013 | McDaniel | |
| 8,618,066 B1 | 12/2013 | McDaniel | |
| 9,012,196 B2 * | 4/2015 | Buthe .................. C12N 9/20 435/183 |
| 2004/0109853 A1 | 6/2004 | McDaniel | |
| 2004/0175407 A1 | 9/2004 | McDaniel | |
| 2004/0241497 A1 | 12/2004 | Sasaki et al. | |
| 2005/0049166 A1 | 3/2005 | Huang | |
| 2005/0147579 A1 | 7/2005 | Schneider et al. | |
| 2006/0110537 A1 | 5/2006 | Huang et al. | |
| 2008/0038241 A1 | 2/2008 | Schasfoort et al. | |
| 2008/0108745 A1 | 5/2008 | Russell et al. | |
| 2008/0119381 A1 | 5/2008 | Wang et al. | |
| 2009/0045056 A1 | 2/2009 | Berberich et al. | |
| 2009/0104086 A1 | 4/2009 | Zax et al. | |

(Continued)

FOREIGN PATENT DOCUMENTS

| AU | 2003304222 A1 | 1/2005 |
|---|---|---|
| AU | 2004257205 A1 | 1/2005 |

(Continued)

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Reactive Surfaces, Ltd., "Bioengineered Enzymes and Peptides," 6 pages (2009).
Yang et al., "lip2, a novel lipase gene cloned from *Aspergillus niger* exhibits enzymatic characteristics distinct from its previously identified family member," Biotechnol. Lett., 32(7):951-6 (2010).
Chen et al., "Candida antarctica Lipase B Chemically Immobilized on Epoxy-Activated Micro- and Nanobeads: Catalysts for Polyester Synthesis," Biomacromolecules, 9(2):463-71, (2008).
Yu et al., "Enhanced activity and enantioselectivity of Candida rugosa lipase immobilized on macroporous adsorptive resins for ibuprofen resolution," Biotechnology Letters, 26(8):629-33 (2004).
Reactive Surfaces, Ltd.; Bioengineered Enzymes and Peptides; pp. 6; 2009.
Yang et al. Biotechnol Lett. Jul. 2010;32(7):951-6. Epub Mar. 8, 2010.

(Continued)

*Primary Examiner* — Christian Fronda
(74) *Attorney, Agent, or Firm* — Dinsmore & Shohl LLP

(57) ABSTRACT

A substrate or coating is provided that includes a lipase with enzymatic activity toward a component of a fingerprint. Also provided is a process for facilitating the removal of fingerprints is provided wherein an inventive substrate or coating including a lipase is capable of enzymatically degrading of one or more components of the fingerprint to facilitate fingerprint removal from the substrate or said coating. Applying heat to the substrate or coating increases the rate of fingerprint removal.

17 Claims, 4 Drawing Sheets

(56) References Cited

U.S. PATENT DOCUMENTS

| | | |
|---|---|---|
| 2009/0238811 A1 | 9/2009 | McDaniel et al. |
| 2010/0210745 A1 | 8/2010 | McDaniel et al. |
| 2010/0248334 A1 | 9/2010 | McDaniel |
| 2010/0269731 A1 | 10/2010 | Tofte Jespersen et al. |
| 2010/0279376 A1 | 11/2010 | Wang et al. |
| 2011/0076738 A1 | 3/2011 | Wang et al. |
| 2011/0240064 A1 | 10/2011 | Wales et al. |
| 2011/0250626 A1 | 10/2011 | Williams et al. |
| 2012/0097194 A1 | 4/2012 | McDaniel et al. |
| 2012/0238005 A1 | 9/2012 | Wieland et al. |
| 2013/0065291 A1 | 3/2013 | Jia et al. |
| 2013/0137159 A1 | 5/2013 | Buthe et al. |

FOREIGN PATENT DOCUMENTS

| | | |
|---|---|---|
| CA | 2538124 A1 | 12/2004 |
| DE | 10341445 | 4/2005 |
| EP | 609691 B1 | 5/1998 |
| EP | 0866103 A1 | 9/1998 |
| EP | 1161502 B1 | 12/2004 |
| EP | 1551927 A1 | 7/2005 |
| EP | 1644452 A2 | 4/2006 |
| EP | 1660596 A1 | 5/2006 |
| EP | 1834759 A1 | 9/2007 |
| FR | 2832145 A1 | 5/2003 |
| GB | 2410249 A | 7/2005 |
| GB | 2430436 A | 3/2007 |
| IL | 167413 A | 12/2010 |
| IL | 174122 A | 9/2011 |
| IL | 173658 A | 4/2012 |
| IL | 208769 A | 4/2012 |
| IL | 214668 A | 1/2013 |
| IL | 214669 A | 1/2013 |
| IL | 214670 A | 1/2013 |
| IL | 214671 A | 1/2013 |
| IL | 214672 A | 1/2013 |
| IL | 218129 A | 9/2013 |
| JP | 3280024 B2 | 4/2002 |
| JP | 2002332739 A | 11/2002 |
| JP | 2007314608 | 12/2007 |
| JP | 2007314609 | 12/2007 |
| KR | 2003054375 | 7/2003 |
| TW | 200493135545 | 11/2007 |
| TW | 200493129104 | 2/2008 |
| WO | 9313256 A1 | 7/1993 |
| WO | 0050521 A1 | 8/2000 |
| WO | 0216521 A1 | 2/2002 |
| WO | 03046090 | 6/2003 |
| WO | 2005/050521 A1 | 6/2005 |
| WO | 2009072738 A1 | 6/2009 |
| WO | 2009155115 A2 | 12/2009 |

OTHER PUBLICATIONS

Chen et al. Biomacromolecules. Feb. 2008;9(2):463-71. Epub Jan. 16, 2008.
Yu et al. Biotechnol Lett. Apr. 2004;26(8):629-33.
Hackeng, T.M., et al., "Total chemical synthesis of enzymaticallly active human type II secretory phospholipase A2," Proc Natl Acad Sci USA, 94(15):7845-50 (1997).
Busca, R., et al., The mutant Asn291® Ser human lipoprotein lipase is associated with reduced catalytic activity and does not influence binding to heparin, FEBS Letters., 367:257-262 (1995).
Oh, S., et al., "Properties of recombinant Rhizomucor miehei lipase with amino acid substitutions of Phe94 in the substrate binding domain." Biotech Lett, 23:563-568 (2001).
O'Sullivan et al., "Methods for the Preparation of Enzyme—Antibody Conjugates for Use in Enzyme Immunoassay," Methods in Enzymology, 73:147-166 (1981).
Block, Steven et al., "New anti-fingerprint coatings," 11th Annual Coatings for Plastics Symposium, Chicago, IL, Dow Corning Corporation, USA (2008).
Zou, Zhongli, et al., "Survey of anti-fingerprint treatment for galvanized steel," Department of Applied Chemistry, Harbin Institute of Technology, Harbin, Peop. Rep. China, 28(3), 1-4 (2008).
Buchbach, Sascha et al., "Self-cleaning surfaces by plasma technology," Oberflaechen Polysurfaces, General Review 49(3), pp. 12-13 (2008).
Buchbach, Sascha et al., "Oberflaechen Polysurfaces," General Review 49(3), pp. 12-13 (2008).
Yu, Wu-gang, et al., "Effects of nano-SiO2 in anti-fingerprint film," Central Iron & Steel Research Institute, 40(11) pp. 56-58, Cailiao Baohu Zazhishe (2007).
Yang, Xingliang et al., "Effect of membrane of chromium-free anti-fingerprint on product attributes of hot-dip galvanized sheet," Maanshan Iron and Steel Co., Ltd., 29(5), pp. 137-140, Shanghaishi Jinshu Xuehui (2007).
Yue, Yuan-guang, et al., "Currrent state and development of anti-fingerprint dope," Xinye Design Company, Central Iron and Steel Research Institute, 40(3), pp. 38-41, Cailiao Baohu Zazhishe (2007).
Block, Steven et al., "PPCJ, Polymers Paint Colour Journal," 198(4526), Dow Corning Corporation, USA (2008).
Busca, R., et al., FEBS Lett., 367:257-262 (1995).
Hackeng, T.M., et al., Proc Natl Acad Sci USA, 94(15):7845-50 (1997).
Erlanger, Methods in Enzymology, 70:85-104 (1980).
O'Sullivan et al., Methods in Enzymology, 73:147-166 (1981).
Oh, S., et al., Biotech Lett, 23:563-568 (2001).
Zou, Zhongli, et al., "Survey of anti-fingerprint treatment for gavanized steel," Department of Applied Chemistry, Harbin Institute of Technology, Harbin, Peop. Rep. China, 28(3), 1-4 (2008).
Johanna Mansfeld et al.; Site-specific and random immobilization of thermolysin-like proteases reflected in the thermal inactivation kinetics; Biotechnol. Appl. Biochem. (2000); pp. 189-195.
Minoru Kumakura et al.; 201. Interaction of Enzyme with Polymer Matrix in Immobilized Enzymes; Helvetica Chimica Acta; vol. 66; Fasc. 7; (1983); pp. 2044-2048.
Jaroslava Turková; Immobilization of Enzymes on Hydroxyalkyl Methacrylate Gels; Immobilization Techniques; Methods in Enzymology; (1976); 344: pp. 66-83.
Masahiro Takagi et al.; Nucleotide Sequence and Promoter Region for the Neutral Protease Gene from *Bacillus stearothermophilus*; Journal of Bacteriology, Sep. 1985, pp. 824-831.
Kuniyo Inouye et al.; Engineering, expression, purification, and production of recombinant thermolysin; Biotechnology Annual Review; vol. 13; ISSN 1387-2656; pp. 43-64.
Novic, S. et al.; Protein-containing hydrophobic coatings and films, Biomaterials, 23: 441-448, 2002.
Drevon, G. et al.; High-Activity Enzyme-Polyurethane Coatings, Biotechnology and Bioengineering, 79(7): 785-794, Sep. 30, 2002.
Mansfeld, et al.: The Stability of Engineered Thermostable Neutral Proteases from Bacillus Stearothermophilus in Organic Solvents and Detergents, Biotechnol. Bioeng. (2007) 97 (4): 672-679.
U.S. Appl. No. 12/643,666, filed Dec. 21, 2009.
U.S. Appl. No. 14/093,347, filed Nov. 29, 2013.
U.S. Appl. No. 14/097,128, filed Dec. 4, 2013.

\* cited by examiner

US 9,428,740 B2

LIPASE-CONTAINING POLYMERIC COATINGS FOR THE FACILITATED REMOVAL OF FINGERPRINTS

CROSS-REFERENCE TO RELATED APPLICATIONS

This patent application is a continuation of U.S. utility patent application Ser. No. 13/757,978 filed Feb. 4, 2013, which is a divisional of U.S. utility patent application Ser. No. 12/820,063, filed Jun. 21, 2010 (now U.S. Pat. No. 8,394,618), the entire contents of which are incorporated herein in their entirety.

FIELD OF THE INVENTION

The present invention relates generally to coating compositions including bioactive substances and methods of their use to facilitate removal of fingerprints. In specific embodiments, the invention relates to methods for fingerprint removal by incorporating lipase into or on polymer composite materials to degrade fingerprint components.

BACKGROUND OF THE INVENTION

Many consumer products such as cell phones, touchscreen displays, automobile door handles, etc., are subject to frequent contact with hands and fingers. As a result, the residue of fingerprints often leaves unpleasant marks on the surface deteriorating the cosmetic appearance of the products.

Prior art approaches aim to reduce the deposition of the fingerprint stains on a surface and facilitate its removal capitalize on the "lotus-effect" where hydrophobic, oleophobic and super-amphiphobic properties are conferred to the surface by polymeric coatings containing appropriate nanocomposites. An exemplary coating contains fluorine and silicon nanocomposites with good roll off properties and very high water and oil contact angles. When used on rough surfaces like sandblasted glass, nanocoatings may act as a filler to provide a fingerprint resistance. A drawback of these "passive" technologies is that they require water-rinsing to finally remove the fingerprints from the surface. In addition, these materials are not suitable for use in high gloss surfaces because the lotus-effect is based on surface roughness.

The photocatalyst $TiO_2$ was used to promote active fingerprint decomposition of fingerprint stains in U.S. Pat. Appl. Publ. 2009/104086. A major drawback to this technology is its limitation to use on inorganic surfaces due to the oxidative impairment of the polymer coating by $TiO_2$.

Therefore, there is a need for new materials or coatings that can actively promote the removal of fingerprints on organic surfaces or in organic coatings and minimize the requirement for maintenance cleaning.

SUMMARY OF THE INVENTION

A composition and method for fingerprint removal from a substrate surface is provided. The method includes associating a lipase with a substrate or a coating such that the lipase is capable of enzymatically degrading a component of a fingerprint.

A method optionally includes heating the substrate or applying heat to the surface of the substrate. In some embodiments heating is at least 5 degrees Celsius above ambient temperature. The substrate or surface thereon is optionally heated to between 40 and 125 degrees Celsius. Heating is optionally continued for at least 30 minutes, illustratively for between 30 minutes to 6 hours.

The composition includes a substrate or coating containing a lipase. The composition optionally includes an organic crosslinkable or non-crosslinkable polymer resin. The resin optionally has a functional group of acetoacetate, acid, amine, carboxyl, epoxy, hydroxyl, isocyanate, silane, vinyl, or combinations thereof. Specific examples of resins include aminoplasts, melamine formaldehydes, carbamates, polyurethanes, polyacrylates, epoxies, polycarbonates, alkyds, vinyls, polyamides, polyolefins, phenolic resins, polyesters, polysiloxanes, or combinations thereof. In particular, a resin is optionally a hydroxyl-functionalized acrylate resin.

A substrate or coating has one or more associated lipase enzymes. A lipase is optionally lipoprotein lipase, acylglycerol lipase, hormone-sensitive lipase, phospholipase A1, phospholipase A2, phospholipase C, phospholipase D, phosphoinositide phospholipase C, a lysophospholipase, or a galactolipase. In particular embodiments, a lipase is a triacylglycerol lipase.

DETAILED DESCRIPTION OF THE PREFERRED EMBODIMENTS

Figure 1:
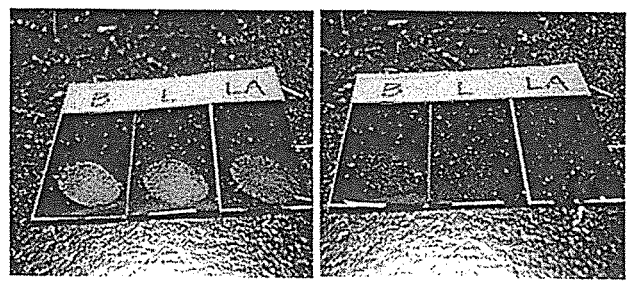
FIG. 1 represents fingerprint removal on a substrate coated with a lipase containing coating.

The following description of embodiment(s) of the invention is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

The present invention is based on the catalytic activity of a lipase enzyme to selectively degrade and volatilize components of fingerprints, thus, promoting active fingerprint removal. Fingerprint stains typically include components of sweat gland secretion and sebum which includes lipids, wax, and cellular debris. Several of the substances of sebum are lipophilic and have low volatility such as squalene and wax esters.

The lipase immobilized in coatings or substrates catalyzes the hydrolysis, esterification, or transesterification of lipids including triacylglycerols, cholesterol esters, and other fingerprint components into smaller molecules. The smaller molecules may have higher volatility than their precursors and more easily vaporize at ambient or elevated temperatures thereby allowing for complete stain removal. Without being limited to one particular theory, it is believed that the resulting degradation products may have lower boiling points or reduced adhesion promoting increased vaporization either upon heating or incubation at ambient temperatures. Thus, the invention has utility as a composition and method for the active removal of fingerprints from surfaces.

The inventive methods and compositions are generally referred to herein as a lipase associated with a substrate for exemplary purposes only. One of ordinary skill in the art appreciates that the description is equally applicable to coatings either on a substrate or prior to application to a substrate.

An inventive method includes providing a substrate or a coating with a lipase or analogue thereof such that the lipase or analogue thereof is enzymatically active and capable of degrading one or more components of a fingerprint. In particular embodiments, a fingerprint is based on bioorganic matter such as that derived from the skin of a subject.

A fingerprint as defined herein is a bioorganic stain, mark, or residue left behind after an organism touches a substrate or coating. A fingerprint is not limited to marks or residue left behind after a substrate is touched by a finger. Other sources of bioorganic stains are illustratively, palms, toes, feet, face, any other skin surface area, hair, stains from fats used in cooking such as cis-fatty acids, or fatty acids from any other source.

A lipase is optionally a lipoprotein lipase, acylglycerol lipase such as triacylglycerol lipase, hormone-sensitive lipase, phospholipase A1, phospholipase A2, phospholipase C, phospholipase D, phosphoinositide phospholipase C, a lysophospholipase, a galactolipase, or combinations or analogues thereof. An analogue of a lipase is optionally a fragment of a lipase. An analogue of a lipase is a polypeptide that has some level of activity toward a natural or synthetic substrate of a lipase. An analogue optionally has between 0.1% and 200% the activity of a wild-type lipase.

Specific examples of lipase include Lipase AP4, Lipase AP6, Lipase AP12, Lipase M-AP5, Lipase M-AP10 and Lipase M-AP20 (manufactured by Amano Pharmaceutical Co., Ltd.), Lipase Saiken (manufactured by Osaka Saikin Kenkyusho), Lipase MY (manufactured by Meito Sangyo), or Lipase B (*Candida antarctica* or *Candida rugosa*). It is also possible to use multiple enzyme preparations having lipase activity. For example, mixed digestive enzyme preparations are operable such as Biodiastase, Biodiastase 500, Biodiastase 700, Biodiastase 1000, Biodiastase 2000, Pancreatin, Pancreatic Digestive Enzyme TA and Pancreatic Digestive Enzyme 8AP (manufactured by Amano Pharmaceutical Co., Ltd.), Biotamylase, Biotamyolase S, Biotalase A-1000, Biotalase P-1000 and Denapsin 10 (manufactured by Nagase Seikagaku Kogyo), Cellulosin AP and Prolicin (manufactured by Ueda Kagaku), Takadiastase (manufactured by Sankyo), Sumizyme (manufactured by Shin Nippon Kagaku Kogyo) and Biotamylase (manufactured by Nagase Sangyo).

A lipase is optionally derived from *Acinetobacter, Aedes aegypti, Anguilla japonica, Antrodia cinnamomea, Arabidopsis rosette, Arabidopsis thaliana, Arxula adeninivorans, Aspergillus niger, Aspergillus oryzae, Aspergillus tamarii, Aureobasidium pullulans, Avena sativa, Bacillus licheniformis, Bacillus sphaericus, Bacillus stearothermophilus, Bacillus subtilis, Bacillus thermocatenulatus, Bacillus thermoleovorans, Bombyx mandarina, Bombyx mori, Bos Taurus, Brassica napus, Brassica rapa, Burkholderia cepacia, Caenorhabditis elegans, Candida albicans, Candida antarctica, Candida deformans, Candida parapsilosis, Candida rugosa, Candida thermophile, Canis domesticus, Chenopodium rubrum, Clostridium beijerinckii, Clostridium botulinum, Clostridium novyi, Danio rerio, Galactomyces geotrichum, Gallus gallus, Geobacillus, Gibberella zeae, Gossypium hirsutum, Homo sapiens, Kurtzmanomyces* sp., *Leishmania infantum, Lycopersicon esculentum* L, *Malassezia furfur, Methanosarcina acetivorans, Mus musculus, Mus spretus, Mycobacterium tuberculosis, Mycoplasma hyopneumoniae, Myxococcus xanthus, Neosartorya fischeri, Oryctolagus cuniculus, Oryza sativa, Penicillium cye/opium, Phlebotomus papatasi, Pseudomonas aeruginosa, Pseudomonas fluorescens, Pseudomonas fragi, Pseudomonas* sp, *Rattus norvegicus, Rhizomucor miehei, Rhizopus oryzae, Rhizopus stolonifer, Ricinus communis, Samia Cynthia ricini, Schizosaccharomyces pombe, Serratia marcescens, Spermophilus tridecemlineatus, Staphylococcus simulans, Staphylococcus xylosus, Sulfolobus solfataricus, Sus scrofa, Thermomyces lanuginosus, Trichomonas vaginalis, Vibrio harveyi, Xenopus laevis, Yarrowia lipolytica*, a combination thereof, or a derivative thereof. It is appreciated that lipases derived from other organisms are similarly operable and are within the scope of the present invention.

A lipase is a "peptide," "polypeptide," and "protein" that are used herein synonymously and are intended to mean a natural or synthetic compound containing two or more amino acids having some level of activity toward a natural or synthetic substrate of a wild-type lipase. A wild-type lipase is a lipase that has an amino acid sequence identical to that found in an organism in nature. An illustrative example of a wild-type lipase is that found at GenBank Accession No. ACL68189 and SEQ ID NO: 1. An exemplary nucleotide sequence encoding a wild-type lipase is found at Accession No. FJ536288 and SEQ ID NO: 2. One of skill in the art recognizes how to modify a nucleotide sequence to alter or create a protein sequence.

```
                                                  (SEQ ID NO: 1)
MFLRREFGAV AALSVLAHAA PAPAPMQRRD ISSTVLDNID

LFAQYSAAAY CSSNIESTGT TLTCDVGNCP LVEAAGATTI

DEFDDSSSYG DPTGFIAVDP TNELIVLSFR GSSDLSNWIA

DLDFGLTSVS SICDGCEMHK GFYEAWEVIA DTITSKVEAA

VSSYPDYTLV FTGHSYGAAL AAVAATVLRN AGYTLDLYNF

GQPRIGNLAL ADYITDQNMG SNYRVTHTDD IVPKLPPELL

GYHHFSPEYW ITSGNDVTVT TSDVTEVVGV DSTDGNDGTL

LDSTTAHRWY TIYISECS
                                                  (SEQ ID NO: 2)
atgtttctcc gcagggaatt tggggctgtt gcagccctat ctgtgctggc ccatgctgct cccgcacctg ctccgatgca gcgtagagac atctcctcta ccgtcttgga caatatcgac ctcttcgccc aatacagtgc agcagcttac tgctcctcca acatcgagtc caccggcacg actctgacct gcgacgtagg caattgccct ctcgtcgagg cagccggtgc cacgaccatc gatgagtttg acgacagcag cagctacggc gacccgacgg ggttcatcgc cgttgacccg acgaacgagt tgatcgttct gtctttccgg ggtagttccg acctctcgaa ctggattgcc gacctagact tcggcctcac ctccgtaagc agcatctgtg atggctgtga gatgcacaag ggcttctatg aggcctggga agtcattgcc gacaccatca catccaaggt ggaggccgct gtctccagct atccggacta caccctcgtg ttcaccggac acagctacgg cgctgcattg gcggctgtcg cggccaccgt actccgcaac gccggataca ctcttgacct gtacaacttc
```

```
        ggccagcccc gtatcggcaa ccttgcttta gctgactaca tcaccgacca aaacatgggc agcaactacc gcgtcacgca caccgacgac atcgtgccta agctgcctcc ggagctgctg ggctaccacc acttcagtcc ggagtactgg atcaccagcg gtaatgatgt gacggtgact acgtcggacg tgaccgaggt tgtgggggtg gattcgacgg atgggaatga cggcacgctg cttgacagta cgactgccca tcggtggtac acgatctaca ttagtgaatg ctcgtag
```

Lipase activity is illustratively defined in units/gram. 1 unit illustratively corresponds to the amount of enzyme that hydrolyzes 1 μmol acetic acid per minute at pH 7.4 and 40° C. using the substrate triacetin (Sigma-Aldrich, St. Louis, Mo., Product No. 90240). The lipase of SEQ ID NO: 1 has an activity of approximately 200 units/gram.

Methods of screening for lipase activity are known and standard in the art. Illustratively, screening for lipase activity in a lipase protein or analogue thereof illustratively includes contacting a lipase or analogue thereof with a natural or synthetic substrate of a lipase and measuring the enzymatic cleavage of the substrate. Illustrative substrates for this purpose include tributyrin and triacetin both of which are cleaved by a triacylglycerol lipase to liberate butyric acid or acetic acid respectively that is readily measured by techniques known in the art.

Amino acids present in a lipase or analogue thereof illustratively include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine; as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutryic acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine. A lipase includes peptides having between 2 and about 1000 amino acids or having a molecular weight in the range of about 150-350,000 Daltons.

A lipase is obtained by any of various methods known in the art illustratively including isolation from a cell or organism, chemical synthesis, expression of a nucleic acid sequence, and partial hydrolysis of proteins. Chemical methods of peptide synthesis are known in the art and include solid phase peptide synthesis and solution phase peptide synthesis or by the method of Hackeng, T M, et al., *Proc Natl Acad Sci USA*, 1997; 94(15):7845-50, the contents of which are incorporated herein by reference. A lipase included in an inventive composition may be a naturally occurring or non-naturally occurring protein. The term "naturally occurring" refers to a protein endogenous to a cell, tissue or organism and includes allelic variations. A non-naturally occurring peptide is synthetic or produced apart from its naturally associated organism or is modified and is not found in an unmodified cell, tissue, or organism.

Modifications and changes can be made in the structure of a lipase and still obtain a molecule having similar characteristics as lipase (e.g., a conservative amino acid substitution). For example, certain amino acids can be substituted for other amino acids in a sequence without appreciable loss of activity or optionally to reduce or increase the activity of an unmodified lipase. Because it is the interactive capacity and nature of a polypeptide that defines that polypeptide's biological functional activity, certain amino acid sequence substitutions can be made in a polypeptide sequence and nevertheless obtain a polypeptide with like or other desired properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution using amino acids whose hydropathic indices are within ±2, those within ±1, and those within ±0.5 are optionally used.

Substitution of like amino acids can also be made on the basis of hydrophilicity. The following hydrophilicity values have been assigned to amino acid residues: arginine (+3.0);

lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain an enzymatically equivalent polypeptide. In such changes, the substitution of amino acids whose hydrophilicity values are within ±2, those within ±1, and those within ±0.5 are optionally used.

Amino acid substitutions are optionally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure, thus, contemplate functional or biological equivalents of a polypeptide as set forth above. In particular, embodiments of the polypeptides can include analogues having about 50%, 60%, 70%, 80%, 90%, 95%, or 99% sequence identity to a wild-type lipase.

It is further appreciated that the above characteristics are optionally taken into account when producing a lipase with reduced or increased enzymatic activity. Illustratively, substitutions in a substrate binding site, exosite, cofactor binding site, catalytic site, or other site in a lipase protein may alter the activity of the enzyme toward a substrate. In considering such substitutions the sequences of other known naturally occurring or non-naturally occurring lipases may be taken into account. Illustratively, the N291S substitution in lipoprotein lipase reduces its enzymatic activity by 30-50 percent. Busca, R. et al, *FEBS Lett.*, 1995; 367:257-262, the contents of which are incorporated herein by reference. Illustratively substitution at amino acid 95 in *Rhizomucor miehei* lipase can produce a 2-3 fold increase in activity toward particular substrates. Similarly substitution at amino acid 94 can produce as much as 6 times the activity of wild-type. Oh, S, et al, Biotech. Lett., 2001; 23: 563-568, the contents of which are incorporated herein by reference. Other substitutions at this or other sites may similarly affect enzymatic activity.

A lipase protein is illustratively recombinant. Methods of cloning, synthesizing or otherwise obtaining nucleic acid sequences encoding a lipase are known and standard in the art that are equally applicable to lipase. Similarly, methods of cell transfection and protein expression are similarly known in the art and are applicable herein. Such methods are illustratively disclosed in Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002, the contents of each of which are incorporated herein by reference.

A lipase may be coexpressed with associated tags, modifications, other proteins such as a fusion peptide, or other modifications or combinations recognized in the art. Illustrative tags include 6× His, FLAG, biotin, ubiquitin, SUMO, or other tag known in the art. A tag is illustratively cleavable such as by linking to lipase or an associated protein via an enzyme cleavage sequence that is cleavable by an enzyme known in the art illustratively including Factor Xa, thrombin, SUMOstar protein as obtainable from Lifesensors, Inc., Malvern, Pa., or trypsin. It is further appreciated that chemical cleavage is similarly operable with an appropriate cleavable linker.

Protein expression is illustratively accomplished from transcription of a lipase nucleic acid sequence, translation of RNA transcribed from the lipase nucleic acid sequence or analogues thereof. Protein expression is optionally performed in a cell based system such as in *E. coli*, Hela cells, or Chinese hamster ovary cells. It is appreciated that cell-free expression systems are similarly operable.

It is recognized that numerous analogues of lipase are operable and within the scope of the present invention including amino acid substitutions, alterations, modifications, or other amino acid changes that increase, decrease, or do not alter the function of the lipase protein sequence. Several post-translational modifications are similarly envisioned as within the scope of the present invention illustratively including incorporation of a non-naturally occurring amino acid, phosphorylation, glycosylation, and addition of pendent groups such as biotinylation, fluorophores, luminophores, radioactive groups, antigens, or other molecules.

An inventive method uses an inventive composition that is one or more lipases incorporated into a substrate itself or into a coating on the substrate. The lipase enzyme is optionally non-covalently associated and/or covalently attached to the substrate or coating material or is otherwise associated therewith such as by bonding to the surface or by intermixing with the substrate/coating material during manufacture such as to produce entrapped lipase. In some embodiments the lipase is covalently attached to the substrate or coating material either by direct covalent interaction between the lipase and one or more components of the substrate or coating material or by association via a link moiety such as that described in U.S. Pat. App. Publ. No. 2008/0119381, the contents of which are incorporated herein by reference.

There are several ways to associate lipase with a substrate or coating. One of which involves the application of covalent bonds. Specifically, free amine groups of the lipase may be covalently bound to an active group of the substrate. Such active groups include alcohol, thiol, aldehyde, carboxylic acid, anhydride, epoxy, ester, or any combination thereof. This method of incorporating lipase delivers unique advantages. First, the covalent bonds tether the lipases permanently to the substrate and thus places them as an integral part of the final composition with much less, if any at all, leakage of the lipase. Second, the covalent bonds provide extended enzyme lifetime. Over time proteins typically lose activity because of the unfolding of their polypeptide chains. Chemical binding such as covalent bonding effectively restricts such unfolding, and thus improves the protein life. The life of a protein is typically determined by comparing the amount of activity reduction of a protein that is free or being physically adsorbed with that of a protein covalently-immobilized over a period of time.

Lipases are optionally uniformly dispersed throughout the substrate network to create a substantially homogenous protein platform. In so doing, lipases may be first modified with polymerizable groups. The modified lipases may be solubilized into organic solvents in the presence of surfactant, and thus engage the subsequent polymerization with monomers such as methyl methacrylate (MMA) or styrene in the organic solution. The resultant composition includes lipase molecules homogeneously dispersed throughout the network.

Lipases are optionally attached to surfaces of a substrate. An attachment of lipases corresponding to approximately 100% surface coverage was achieved with polystyrene particles with diameters range from 100 to 1000 nm.

Chemical methods of lipase attachment to materials will naturally vary depending on the functional groups present in the lipase and in the material components. Many such methods exist. For example, methods of attaching proteins (such as enzymes) to other substances are described in O'Sullivan et al, *Methods in Enzymology,* 1981; 73:147-166 and Erlanger, *Methods in Enzymology,* 1980; 70:85-104, each of which are herein incorporated herein by reference.

Lipases are optionally present in a coating that is layered upon a substrate wherein the lipase is optionally entrapped in the coating material, admixed therewith, modified and integrated into the coating material or layered upon a coating similar to the mechanisms described for interactions between a lipase and substrate material.

Materials operable for interactions with a lipase to form an active substrate or coating illustratively include organic polymeric materials. The combination of these materials and a lipase form a protein-polymer composite material that is used as a substrate material or a coating.

Methods of preparing protein-polymer composite materials illustratively include use of aqueous solutions of lipase and non-aqueous organic solvent-borne polymers to produce bioactive organic solvent-borne protein-polymer composite materials.

Methods of preparing protein-polymer composite materials are illustratively characterized by dispersion of lipase in solvent-borne resin prior to curing and in the composite materials. Lipases are optionally dispersed in the protein-polymer composite material such that the lipases are unassociated with other bioactive proteins and/or form relatively small particles of associated proteins. Illustratively, the average particle size of lipase particles in the protein-polymer composite material is less than 10 μm (average diameter) such as in the range of 1 nm to 10 μm, inclusive.

Curable protein-polymer compositions are optionally two-component solvent-borne (2K SB) compositions. Optionally, one component systems (1K) are similarly operable. Illustratively, a lipase is entrapped in a coating material such as a latex or enamel paint, varnish, polyurethane gels, or other coating materials. Illustrative examples of incorporating enzymes into paints are presented in U.S. Pat. No. 5,998,200, the contents of which are incorporated herein by reference.

In two-component (2K) systems the two components are optionally mixed shortly before use, for instance, application of the curable protein-polymer composition to a substrate to form a lipase containing coating such as a bioactive clear coat. Generally described, the first component contains a crosslinkable polymer resin and the second component contains a crosslinker. Thus, the emulsion is a first component containing a crosslinkable resin and the crosslinker is a second component, mixed together to produce the curable protein-polymer composition.

A polymer resin included in methods and compositions of the present invention can be any film-forming polymer useful in coating or substrate compositions, illustratively clear coat compositions. Such polymers illustratively include, aminoplasts, melamine formaldehydes, carbamates, polyurethanes, polyacrylates, epoxies, polycarbonates, alkyds, vinyls, polyamides, polyolefins, phenolic resins, polyesters, polysiloxanes; and combinations of any of these or other polymers.

In particular embodiments, a polymer resin is crosslinkable. Illustratively, a crosslinkable polymer has a functional group characteristic of a crosslinkable polymer. Examples of such functional groups illustratively include acetoacetate, acid, amine, carboxyl, epoxy, hydroxyl, isocyanate, silane, vinyl, other operable functional groups, and combinations thereof.

Examples of organic crosslinkable polymer resins include aminoplasts, melamine formaldehydes, carbamates, polyurethanes, polyacrylates, epoxies, polycarbonates, alkyds, vinyls, polyamides, polyolefins, phenolic resins, polyesters, polysiloxanes, or combinations thereof.

A crosslinking agent is optionally included in the composition. The particular crosslinker selected depends on the particular polymer resin used. Non-limiting examples of crosslinkers include compounds having functional groups such as isocyanate functional groups, epoxy functional groups, aldehyde functional groups, and acid functionality.

In particular embodiments of protein-polyurethane composite materials, a polymer resin is a hydroxyl-functional acrylic polymer and the crosslinker is a polyisocyanate.

A polyisocyanate, optionally a diisocyanate, is a crosslinker reacted with the hydroxyl-functional acrylic polymer according to embodiments of the present invention. Aliphatic polyisocyanates are preferred polyisocyanates used in processes for making protein-polymer composite materials for clearcoat applications such as in automotive clearcoat applications. Non-limiting examples of aliphatic polyisocyanates include 1,4-butylene diisocyanate, 1,4-cyclohexane diisocyanate, 1,2-diisocyanatopropane, 1,3-diisocyanatopropane, ethylene diisocyanate, lysine diisocyanate, 1,4-methylene bis (cyclohexyl isocyanate), diphenylmethane 4,4'-diisocyanate, an isocyanurate of diphenylmethane 4,4'-diisocyanate, methylenebis-4,4'-isocyanatocyclohexane, 1,6-hexamethylene diisocyanate, an isocyanurate of 1,6-hexamethylene diisocyanate, isophorone diisocyanate, an isocyanurate of isophorone diisocyanate, p-phenylene diisocyanate, toluene diisocyanate, an isocyanurate of toluene diisocyanate, triphenylmethane 4,4',4"-triisocyanate, tetramethyl xylene diisocyanate, and meta-xylene diisocyanate.

Curing modalities are those typically used for conventional curable polymer compositions.

Lipase-polymer composite materials used in embodiments of the present invention are optionally thermoset protein-polymer composite materials. For example, a substrate or coating material is optionally cured by thermal curing. A thermal polymerization initiator is optionally included in a curable composition. Thermal polymerization initiators illustratively include free radical initiators such as organic peroxides and azo compounds. Examples of organic peroxide thermal initiators illustratively include benzoyl peroxide, dicumylperoxide, and lauryl peroxide. An exemplary azo compound thermal initiator is 2,2'-azobisisobutyronitrile.

Conventional curing temperatures and curing times can be used in processes according to embodiments of the present invention. For example, the curing time at specific temperatures, or under particular curing conditions, is determined by the criteria that the cross-linker functional groups are reduced to less than 5% of the total present before curing. Cross-linker functional groups can be quantitatively characterized by FT-IR or other suitable method. For example, the curing time at specific temperatures, or under particular curing conditions, for a polyurethane protein-polymer composite of the present invention can be determined by the criteria that the cross-linker functional group NCO is reduced to less than 5% of the total present before curing. The NCO group can be quantitatively characterized by FT-IR. Additional methods for assessing the extent of curing for particular resins are well-known in the art. Illustratively, curing may include evaporation of a solvent or by exposure to actinic radiation, such as ultraviolet, electron beam, microwave, visible, infrared, or gamma radiation.

One or more additives are optionally included for modifying the properties of the lipase-polymer composite material and/or the admixture of organic solvent and polymer resin, the aqueous lipase solution, the emulsion, and/or the curable composition. Illustrative examples of such additives include a UV absorbing agent, a plasticizer, a wetting agent, a preservative, a surfactant, a lubricant, a pigment, a filler, and an additive such as an additive to increase sag resistance.

A substrate or coating including a lipase is illustratively an admixture of a polymer resin, a surfactant and a non-aqueous organic solvent, mixed to produce an emulsion. The term "surfactant" refers to a surface active agent that reduces the surface tension of a liquid in which it is dissolved, or that reduces interfacial tension between two liquids or between a liquid and a solid.

Surfactants used can be of any variety including amphoteric, silicone-based, fluorosurfactants, anionic, cationic and nonionic such as described in K. R. Lange, Surfactants: A Practical Handbook, Hanser Gardner Publications, 1999; and R. M. Hill, Silicone Surfactants, CRC Press, 1999. Examples of anionic surfactants include alkyl sulfonates, alkylaryl sulfonates, alkyl sulfates, alkyl and alkylaryl disulfonates, sulfonated fatty acids, sulfates of hydroxyalkanols, sulfosuccinic acid esters, sulfates and sulfonates of polyethoxylated alkanols and alkylphenols. Examples of cationic surfactants include quaternary surfactants and amineoxides. Examples of nonionic surfactants include alkoxylates, alkanolamides, fatty acid esters of sorbitol or manitol, and alkyl glucamides. Examples of silicone-based surfactants include siloxane polyoxyalkylene copolymers.

When a surface which is optionally a substrate or a coated substrate, is contacted with a fingerprint, the lipase enzyme or combinations of enzymes contact the fingerprint, or components thereof. The contacting allows the enzymatic activity of the substrate or coating to interact with and enzymatically alter the components of the fingerprint improving their removal from the substrate or coating.

It is appreciated that the inventive methods of facilitating fingerprint removal will function at any temperature whereby the lipase is active. Optionally, the inventive method is performed at 4° C. Optionally, an inventive method is performed at 25° C. Optionally, an inventive process is performed at ambient temperature. Some embodiments are performed between 40° C. and 120° C.

An inventive method optionally includes heating the substrate itself or applying heat to the surface of the substrate. Heating is defined as increasing the surface temperature of a substrate/coating to a level higher than the ambient temperature. In some embodiments heating is raising the surface temperature by at least 5° C. Heating is optionally raised by exposure to sunlight or other heat source. The surface temperature is optionally raised to such a level that the breakdown products volatilize to the point of no visual material remaining on the substrate within 24 hours. Optionally, the temperature is raised to such a level that the breakdown products are removed to the point of no visual material remaining on the substrate within 0.5 to 3 hours, inclusive. Optionally, the substrate surface temperature is increased to between 40° C. and 125° C., inclusive.

Heat is optionally applied continuously or intermittently. Heat is optionally applied until the breakdown products volatilize to the point of no visual material remaining on the substrate. Optionally, heat is applied for at least 30 minutes. In some embodiments, heat is applied for between 30 minutes to 6 hours, inclusive.

The presence of lipase combined with the material of a substrate or a coating on a substrate, optionally, with applied heat, breaks down fingerprint stains for facilitated fingerprint removal.

Various aspects of the present invention are illustrated by the following non-limiting examples. The examples are for illustrative purposes and are not a limitation on any practice of the present invention. It will be understood that variations and modifications can be made without departing from the spirit and scope of the invention.

Example 1

Production of lipase containing material operable for coating a substrate.

Materials: Polyacrylate resin Desmophen A870 BA, and the hexamethylene diisocyanate (HDI) based polyfunctional aliphatic polyisocyanate resin Desmodur N 3600, the polyester resin Bayhydrol XP 7093, and Bayhydur 302 are obtained from Bayer Corp. (Pittsburgh, Pa.). The surfactant BYK-333 is obtained from BYK-Chemie (Wallingford, Conn.). α-Amylase KLEISTASE SD80 from *Bacillus subtilis* (EC 3.2.1.1), lipase PS from *Burkholderia cepacia*, and Lipase AP12 from *Aspergillus niger* are obtained from Amano Enzyme Inc. (Nagoya, Japan). Butyl acetate, Bradford reagent, bovine serum albumin (BSA) from bovine serum, starch from potatoes, starch from wheat, maltose, sodium potassium tartrate, 3,5-dinitrosalicylic acid, $Na_2(PO_4)$, NaCl, $K_2(PO_4)$, casein, trichloroacetic acid, Folin & Ciocalteu's phenol reagent, $Na_2(CO_3)$, sodium acetate, calcium acetate, tyrosine, p-nitrophenyl palmitate, ethanol, iodine, glucose, maltose, maltotriose, maltohexose, dextrin with different molecular weight (10 kDa, 40 kDa) were obtained from Sigma Chemical Co., St. Louis, Mo., U.S.A. Aluminum panels and 8-path wet film applicators are obtained from Paul N. Gardner Company, Inc. (Pompano Beach, Fla.).

Enzyme preparation: Lipase AP12 is subjected to purification from a 150 mL solution containing 7.5 g crude lipase powder in DI water at a protein concentration of about 5 mg/mL (determined by the Bradford method). All solutions are kept on ice. Ultrafiltration is performed using a 150 mL Amicon cell (Millipore, Billerica, Mass.) at a pressure of 55 psi using a 30 kDa cut-off membrane. Ultrafiltration is repeated 3 times by adding DI water to the remaining concentrated solution to a volume of 150 mL after each run. The final remaining purified protein solution is used to prepare coatings typically at a lipase concentration of 200 mg/mL.

Incorporation of lipase in to form protein-polymer coating: Solvent-borne two-component polyurethane (PU) is formed by the polymerization of Desmophen A 870 BA and Desmodur N 3600 at a weight ratio of 2.6:1 of Desmophen A 870 BA to Desmodur N 3600. Typically, 2.1 g of Desmophen A 870 BA (solid content of 70 wt %), 0.0167 g of BYK-333 dissolved in 100 µl of n-butanol, and 0.5 mL of butyl acetate are mixed in a 20 mL vial. 600 µl of 200 mg/mL purified lipase enzyme solution is added and mixed for 1 minute to form a white emulsion. Subsequently, 0.8 g of Desmodur N 3600 is added and mixed manually for 1 minute. The resulting curable protein-polymer solution is then applied to aluminum testing panels via drawdown using an 8-path applicator. The resulting coating is cured at 80° C. for 24 hours.

Example 2

Fingerprint removal: The lipase containing coated panels of Example 1 are loaded with human fingerprints after touching the skin of the face or forearms. Fingerprinted panels are incubated at room temperature for at least 24 hours. A control panel is coated with the coating of Example 1 that is free of enzyme. After this first incubation period, the coated substrate is incubated in an oven at a temperature of 65° C. or higher for 1 to 6 hours.

FIG. 1 demonstrates that incubation of the enzyme coated panels at 65° C. for two hours facilitates complete removal of fingerprints. (B: control; L: lipase; LA: combined lipase and amylase in coating.)

Example 3

Figure 2:
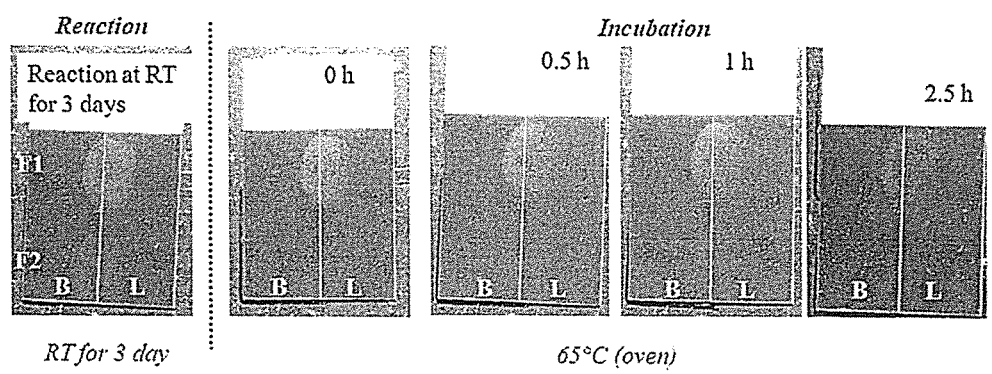
FIG. 2 represents increased fingerprint removal rates on a plate coated with a lipase containing coating.
Figure 3:
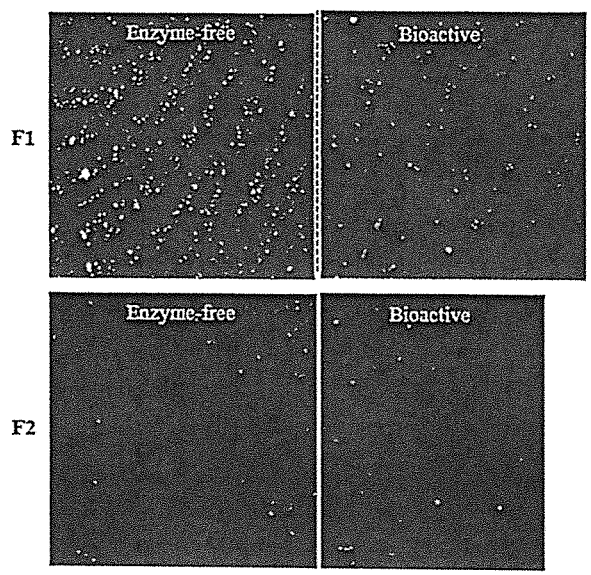
FIG. 3 represents similar removal rates of fingerprints from multiple sources.
Figure 4:
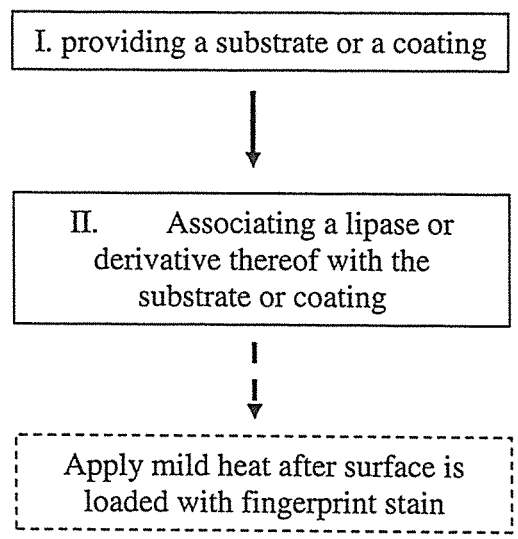
FIG. 4 represents a schematic of an inventive method.

The rate of fingerprint removal is faster in an enzyme containing substrate than control. FIG. 2 demonstrates aluminum plates coated with control or enzyme containing protein-polymer coatings as described in Example 1 where a fingerprint is loaded at the interface between the two coatings as described in Example 2. FIG. 2A demonstrates the remaining fingerprint after incubation at ambient temperature for 3 days. The plates are subsequently incubated for 2.5 hours at 65° C. and photographs are taken at various intervals as illustrated in FIG. 2B. FIG. 3 demonstrates that the increased rate of fingerprint removal is independent of the source of the fingerprints.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:
1. A composition for facilitating fingerprint removal comprising:
   a polymeric coating material formed from crosslinkable non-aqueous organic solvent-borne resin; and
   a lipase capable of degrading a fingerprint component, said lipase associated with said coating material so as to be capable of facilitating fingerprint removal when said coating material is contacted by a fingerprint;
   with the proviso that when the lipase is a triacylglycerol lipase, the triacylglycerol lipase is from *Acinetobacter, Aedes aegypti, Anguilla japonica, Antrodia cinnamomea, Arabidopsis rosette, Arabidopsis thaliana, Arxula adeninivorans, Aspergillus oryzae, Aspergillus tamarii, Aureobasidium pullulans, Avena sativa, Bacillus licheniformis, Bacillus sphaericus, Bacillus stearothermophilus, Bacillus subtilis, Bacillus thermocatenulatus, Bacillus thermoleovorans, Bombyx mandarina, Bombyx mori, Bos Taurus, Brassica napus, Brassica rapa, Burkholderia cepacia, Caenorhabditis elegans, Candida albicans, Candida antarctica, Candida deformans, Candida parapsilosis, Candida rugosa, Candida thermophila, Canis domesticus, Chenopodium rubrum, Clostridium beijerinckii, Clostridium botulinum, Clostridium novyi, Danio rerio, Galactomyces geotrichum, Gallus gallus, Geobacillus, Gibberella zeae,*

*Gossypium hirsutum, Homo sapiens, Kurtzmanomyces* sp., *Leishmania infantum, Lycopersicon esculentum* L, *Malassezia furfur, Methanosarcina acetivorans, Mus musculus, Mus spretus, Mycobacterium tuberculosis, Mycoplasma hyopneumoniae, Myxococcus xanthus, Neosartorya fischeri, Oryctolagus cuniculus, Oryza sativa, Penicillium cye/opium, Phlebotomus papatasi, Pseudomonas aeruginosa, Pseudomonas fluorescens, Pseudomonas fragi, Pseudomonas* sp, *Rattus norvegicus, Rhizomucor miehei, Rhizopus oryzae, Rhizopus stolonifer, Ricinus communis, Samia Cynthia ricini, Schizosaccharomyces pombe, Serratia marcescens, Spermophilus tridecemlineatus, Staphylococcus simulans, Staphylococcus xylosus, Sulfolobus solfataricus, Sus scrofa, Thermomyces lanuginosus, Trichomonas vaginalis, Vibrio harveyi, Xenopus laevis,* or *Yarrowia lipolytica;* said composition uniformly coated onto a substrate.

2. The composition of claim 1 wherein said coating comprises an organic crosslinkable polymer resin having a functional group of acetoacetate, acid, amine, carboxyl, epoxy, hydroxyl, isocyanate, silane, vinyl, or combinations thereof.

3. The composition of claim 2 wherein said organic crosslinkable polymer resin is aminoplasts, melamine formaldehydes, carbamates, polyurethanes, polyacrylates, epoxies, polycarbonates, alkyds, vinyls, polyamides, polyolefins, phenolic resins, polyesters, polysiloxanes, or combinations thereof.

4. The composition of claim 2 wherein said organic crosslinkable polymer is a hydroxyl-functionalized acrylate resin.

5. The composition of claim 1 wherein said lipase is lipoprotein lipase, acylglycerol lipase, hormone-sensitive lipase, phospholipase A1, phospholipase A2, phospholipase C, phospholipase D, phosphoinositide phospholipase C, a lysophospholipase, or a galactolipase.

6. The composition of claim 1 wherein said lipase is a triacylglycerol lipase.

7. The composition of claim 1 wherein said lipase is covalently associated with said coating.

8. A composition for facilitating fingerprint removal comprising:
a polymeric substrate formed from crosslinkable non-aqueous organic solvent-borne resin;
a lipase capable of degrading a fingerprint component, said lipase associated with said substrate so as to be capable of degrading a fingerprint contacting said substrate; and
a fingerprint, said fingerprint contacting said substrate and said lipase;
with the proviso that when the lipase is triacylglycerol lipase, the triacylglycerol lipase is from *Acinetobacter, Aedes aegypti, Anguilla japonica, Antrodia cinnamomea, Arabidopsis rosette, Arabidopsis thaliana, Arxula adeninivorans, Aspergillus oryzae, Aspergillus tamarii, Aureobasidium pullulans, Avena sativa, Bacillus licheniformis, Bacillus sphaericus, Bacillus stearothermophilus, Bacillus subtilis, Bacillus thermocatenulatus, Bacillus thermoleovorans, Bombyx mandarina, Bombyx mori, Bos Taurus, Brassica napus, Brassica rapa, Burkholderia cepacia, Caenorhabditis elegans, Candida albicans, Candida antarctica, Candida deformans, Candida parapsilosis, Candida rugosa, Candida thermophila, Canis domesticus, Chenopodium rubrum, Clostridium beijerinckii, Clostridium botulinum, Clostridium novyi, Danio rerio, Galactomyces geotrichum, Gallus gallus, Geobacillus, Gibberella zeae, Gossypium hirsutum, Homo sapiens, Kurtzmanomyces* sp., *Leishmania infantum, Lycopersicon esculentum* L, *Malassezia furfur, Methanosarcina acetivorans, Mus musculus, Mus spretus, Mycobacterium tuberculosis, Mycoplasma hyopneumoniae, Myxococcus xanthus, Neosartorya fischeri, Oryctolagus cuniculus, Oryza sativa, Penicillium cye/opium, Phlebotomus papatasi, Pseudomonas aeruginosa, Pseudomonas fluorescens, Pseudomonas fragi, Pseudomonas* sp, *Rattus norvegicus, Rhizomucor miehei, Rhizopus oryzae, Rhizopus stolonifer, Ricinus communis, Samia Cynthia ricini, Schizosaccharomyces pombe, Serratia marcescens, Spermophilus tridecemlineatus, Staphylococcus simulans, Staphylococcus xylosus, Sulfolobus solfataricus, Sus scrota, Thermomyces lanuginosus, Trichomonas vaginalis, Vibrio harveyi, Xenopus laevis,* or *Yarrowia lipolytica.*

9. The composition of claim 8 wherein said substrate comprises an organic crosslinkable polymer resin having a functional group of acetoacetate, acid, amine, carboxyl, epoxy, hydroxyl, isocyanate, silane, vinyl, or combinations thereof.

10. The composition of claim 9 wherein said organic crosslinkable polymer resin is aminoplasts, melamine formaldehydes, carbamates, polyurethanes, polyacrylates, epoxies, polycarbonates, alkyds, vinyls, polyamides, polyolefins, phenolic resins, polyesters, polysiloxanes, or combinations thereof.

11. The composition of claim 9 wherein said organic crosslinkable polymer is a hydroxyl-functionalized acrylate resin.

12. The composition of claim 8 wherein said lipase is lipoprotein lipase, acylglycerol lipase, hormone-sensitive lipase, phospholipase A1, phospholipase A2, phospholipase C, phospholipase D, phosphoinositide phospholipase C, a lysophospholipase, or a galactolipase.

13. The composition of claim 8 wherein said lipase is a triacylglycerol lipase.

14. The composition of claim 8 wherein said lipase is covalently associated with said substrate.

15. A curable composition for facilitating fingerprint removal comprising:
a lipase; and
a solvent-borne two-component polyurethane coating material;
said lipase dispersed into said coating by covalent interaction with said coating material so as to be capable of degrading a fingerprint when said coating is contacted by a fingerprint;
with the proviso that when the lipase is triacylglycerol lipase, the triacylglycerol lipase is from *Acinetobacter, Aedes aegypti, Anguilla japonica, Antrodia cinnamomea, Arabidopsis rosette, Arabidopsis thaliana, Arxula adeninivorans, Aspergillus oryzae, Aspergillus tamarii, Aureobasidium pullulans, Avena sativa, Bacillus licheniformis, Bacillus sphaericus, Bacillus stearothermophilus, Bacillus subtilis, Bacillus thermocatenulatus, Bacillus thermoleovorans, Bombyx mandarina, Bombyx mori, Bos Taurus, Brassica napus, Brassica rapa, Burkholderia cepacia, Caenorhabditis elegans, Candida albicans, Candida antarctica, Candida deformans, Candida parapsilosis, Candida rugosa, Candida thermophila, Canis domesticus, Chenopodium rubrum, Clostridium beijerinckii, Clostridium botulinum, Clostridium novyi, Danio rerio, Galactomyces geotrichum, Gallus gallus, Geobacillus, Gibberella zeae,*

*Gossypium hirsutum, Homo sapiens, Kurtzmanomyces* sp., *Leishmania infantum, Lycopersicon esculentum* L, *Malassezia furfur, Methanosarcina acetivorans, Mus musculus, Mus spretus, Mycobacterium tuberculosis, Mycoplasma hyopneumoniae, Myxococcus xanthus, Neosartorya fischeri, Oryctolagus cuniculus, Oryza sativa, Penicillium cye/opium, Phlebotomus papatasi, Pseudomonas aeruginosa, Pseudomonas fluorescens, Pseudomonas fragi, Pseudomonas* sp, *Rattus norvegicus, Rhizomucor miehei, Rhizopus oryzae, Rhizopus stolonifer, Ricinus communis, Samia Cynthia ricini, Schizosaccharomyces pombe, Serratia marcescens, Spermophilus tridecemlineatus, Staphylococcus simulans, Staphylococcus xylosus, Sulfolobus solfataricus, Sus scrofa, Thermomyces lanuginosus, Trichomonas vaginalis, Vibrio harveyi, Xenopus laevis*, or *Yarrowia lipolytica.*

16. The composition of claim 15 wherein said lipase is lipoprotein lipase, acylglycerol lipase, hormone-sensitive lipase, phospholipase A1, phospholipase A2, phospholipase C, phospholipase D, phosphoinositide phospholipase C, a lysophospholipase, or a galactolipase.

17. The composition of claim 15 wherein said lipase is a triacylglycerol lipase.

* * * * *

```
SEQUENCE LISTING

<160> NUMBER OF SEQ ID NOS: 2

<210> SEQ ID NO 1
<211> LENGTH: 298
<212> TYPE: PRT
<213> ORGANISM: Aspergillus niger

<400> SEQUENCE: 1

Met Phe Leu Arg Arg Glu Phe Gly Ala Val Ala Ala Leu Ser Val Leu
1               5                   10                  15

Ala His Ala Ala Pro Ala Pro Ala Pro Met Gln Arg Arg Asp Ile Ser
            20                  25                  30

Ser Thr Val Leu Asp Asn Ile Asp Leu Phe Ala Gln Tyr Ser Ala Ala
        35                  40                  45

Ala Tyr Cys Ser Ser Asn Ile Glu Ser Thr Gly Thr Thr Leu Thr Cys
    50                  55                  60

Asp Val Gly Asn Cys Pro Leu Val Glu Ala Ala Gly Ala Thr Thr Ile
65                  70                  75                  80

Asp Glu Phe Asp Asp Ser Ser Ser Tyr Gly Asp Pro Thr Gly Phe Ile
                85                  90                  95

Ala Val Asp Pro Thr Asn Glu Leu Ile Val Leu Ser Phe Arg Gly Ser
            100                 105                 110

Ser Asp Leu Ser Asn Trp Ile Ala Asp Leu Asp Phe Gly Leu Thr Ser
        115                 120                 125

Val Ser Ser Ile Cys Asp Gly Cys Glu Met His Lys Gly Phe Tyr Glu
    130                 135                 140

Ala Trp Glu Val Ile Ala Asp Thr Ile Thr Ser Lys Val Glu Ala Ala
145                 150                 155                 160

Val Ser Ser Tyr Pro Asp Tyr Thr Leu Val Phe Thr Gly His Ser Tyr
                165                 170                 175
```

-continued

```
Gly Ala Ala Leu Ala Ala Val Ala Ala Thr Val Leu Arg Asn Ala Gly
            180                 185                 190
Tyr Thr Leu Asp Leu Tyr Asn Phe Gly Gln Pro Arg Ile Gly Asn Leu
        195                 200                 205
Ala Leu Ala Asp Tyr Ile Thr Asp Gln Asn Met Gly Ser Asn Tyr Arg
    210                 215                 220
Val Thr His Thr Asp Asp Ile Val Pro Lys Leu Pro Glu Leu Leu
225                 230                 235                 240
Gly Tyr His His Phe Ser Pro Glu Tyr Trp Ile Thr Ser Gly Asn Asp
                245                 250                 255
Val Thr Val Thr Thr Ser Asp Val Thr Glu Val Val Gly Val Asp Ser
            260                 265                 270
Thr Asp Gly Asn Asp Gly Thr Leu Leu Asp Ser Thr Thr Ala His Arg
        275                 280                 285
Trp Tyr Thr Ile Tyr Ile Ser Glu Cys Ser
    290                 295
```

<210> SEQ ID NO 2
<211> LENGTH: 897
<212> TYPE: DNA
<213> ORGANISM: Aspergillus niger

<400> SEQUENCE: 2

```
atgtttctcc gcagggaatt tggggctgtt gcagccctat ctgtgctggc ccatgctgct      60
cccgcacctg ctccgatgca gcgtagagac atctcctcta ccgtcttgga caatatcgac    120
ctcttcgccc aatacagtgc agcagcttac tgctcctcca acatcgagtc caccggcacg    180
actctgacct gcgacgtagg caattgccct ctcgtcgagg cagccggtgc cacgaccatc    240
gatgagtttg acgacagcag cagctacggc gacccgacgg ggttcatcgc cgttgacccg    300
acgaacgagt tgatcgttct gtctttccgg ggtagttccg acctctcgaa ctggattgcc    360
gacctagact tcggcctcac ctccgtaagc agcatctgtg atggctgtga gatgcacaag    420
ggcttctatg aggcctggga agtcattgcc gacaccatca catccaaggt ggaggccgct    480
gtctccagct atccggacta caccctcgtg ttcaccggac acagctacgg cgctgcattg    540
gcggctgtcg cggccaccgt actccgcaac gccggataca ctcttgacct gtacaacttc    600
ggccagcccc gtatcggcaa ccttgcttta gctgactaca tcaccgacca aaacatgggc    660
agcaactacc gcgtcacgca caccgacgac atcgtgccta agctgcctcc ggagctgctg    720
ggctaccacc acttcagtcc ggagtactgg atcaccagcg gtaatgatgt gacggtgact    780
acgtcggacg tgaccgaggt tgtggggtg gattcgacgg atgggaatga cggcacgctg    840
cttgacagta cgactgccca tcggtggtac acgatctaca ttagtgaatg ctcgtag       897
```